United States Patent
Vignon et al.

(10) Patent No.: US 11,786,222 B2
(45) Date of Patent: Oct. 17, 2023

(54) SYSTEM AND METHOD FOR ACQUISITION TRIGGERING FOR CARDIAC ELASTOGRAPHY

(71) Applicant: KONINKLIJKE PHILIPS N.V., Eindhoven (NL)

(72) Inventors: Francois Guy Gerard Marie Vignon, Andover, MA (US); Carolina Amador Carrascal, Everett, MA (US); Seungsoo Kim, Andover, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 187 days.

(21) Appl. No.: 17/603,630

(22) PCT Filed: Apr. 17, 2020

(86) PCT No.: PCT/EP2020/060813
§ 371 (c)(1),
(2) Date: Oct. 14, 2021

(87) PCT Pub. No.: WO2020/212551
PCT Pub. Date: Oct. 22, 2020

(65) Prior Publication Data
US 2022/0192640 A1 Jun. 23, 2022

Related U.S. Application Data

(60) Provisional application No. 62/835,565, filed on Apr. 18, 2019.

(51) Int. Cl.
*A61B 8/00* (2006.01)
*A61B 8/08* (2006.01)
*G01S 7/52* (2006.01)
*G01S 15/89* (2006.01)

(52) U.S. Cl.
CPC ............ *A61B 8/543* (2013.01); *A61B 8/0883* (2013.01); *A61B 8/485* (2013.01); *G01S 7/52073* (2013.01); *G01S 7/52074* (2013.01); *G01S 15/899* (2013.01); *G01S 15/8993* (2013.01); *A61B 8/488* (2013.01); *G01S 15/8979* (2013.01)

(58) Field of Classification Search
CPC ....... A61B 8/543; A61B 8/0883; A61B 8/485; A61B 8/488; G01S 7/52073; G01S 7/52074; G01S 15/899; G01S 15/8993; G01S 15/8979
See application file for complete search history.

(56) References Cited

U.S. PATENT DOCUMENTS

2015/0119710 A1   4/2015   Kawae et al.
2015/0272547 A1   10/2015   Freiburger et al.

OTHER PUBLICATIONS

PCT/EP2020/060813 ISR & Written Opinion, dated Aug. 28, 2020.
(Continued)

*Primary Examiner* — Dixomara Vargas

(57) ABSTRACT

Systems and methods for triggering the acquisition of elastography measurements based on motion data are disclosed. Motion data may be acquired by Doppler mode imaging in some embodiments. The motion data may be used to generate a trigger signal. The trigger signal may be provided to a transmit controller. The transmit controller may cause an ultrasound transducer to acquire elastography measurements responsive to the trigger signal.

15 Claims, 9 Drawing Sheets

(56) References Cited

OTHER PUBLICATIONS

Konofagou et al: "Myocardial Elastography—A Feasibility Study in Vivo"; Ultrasound in Med. & Biol. vol. 28, No. 4, pp. 475-482, 2002.
Song et al: Quantitative Assessment of Left Ventricular Distolic Stiffness Using Cardiac Shear Wave Elastography: J Ultrasound Med 2016, 35:1419-1427.
Varghese et al: "Ultrasonic Imaging of Myocardial Strain Using Cardiac Elastography"; Ultrasonic Imaging 25, pp. 1-16, 2003.
Vignon et al: "Fast Frame Rate 2D Cardiac Deformation Imaging Based on RF Data: What Do We Gain?"; IEEE 2017.

SYSTEM AND METHOD FOR ACQUISITION TRIGGERING FOR CARDIAC ELASTOGRAPHY

CROSS-REFERENCE TO PRIOR APPLICATIONS

This application is the U.S. National Phase application under 35 U.S.C. § 371 of International Application No. PCT/EP2020/060813, filed on Apr. 17, 2020, which claims the benefit of U.S. Provisional Patent Application No. 62/835,565, filed on Apr. 18, 2019. These applications are hereby incorporated by reference herein.

TECHNICAL FIELD

The present disclosure pertains to ultrasound systems and methods for shear wave elastography, and more specifically to an ultrasound system and method configured to use motion-based triggering for elastography measurements.

BACKGROUND

Ultrasound Shear Wave Elastography (SWE), evaluating tissue elasticity by measuring shear wave speed, has become widely accepted as a non-invasive and quantitative diagnostic modality. Most SWE systems induce shear waves using Acoustic Radiation Force (ARF). In a typical exemplary system, an initial, long ultrasound pulse, referred to as a push pulse, is applied to a tissue via ARF. The tissue may respond to the force of the push pulse by deforming. This deformation propagates through the tissue as one or more waves, referred to as shear waves. The propagation of the shear wave or waves through the tissue is monitored by additional ultrasound pulses, referred to as tracking pulses.

Based on one or more factors (e.g., shear wave velocity, shear wave magnitude, and/or maximum propagation distance), a stiffness value of the tissue is calculated. An example of a stiffness value is the Young's modulus (E), typically measured in kPa. One method of calculating the elastic modulus is $E=3\rho(V_s)^2$, where $V_s$ is the shear wave propagation velocity in m/s and p is tissue density in $kg/m^3$. Other methods of calculating a stiffness value of the tissue may be used. For example, the shear wave propagation velocity alone may be used as a measure of tissue stiffness. In some cases an expected value for p may be estimated as the density of water. In other cases only a differential measurement may be used and the expected value of ρ will factored out of any measurement.

Tissue stiffness measurements (e.g., elastography measurements) may be useful in disease diagnosis and/or monitoring. For example, in cirrhosis of the liver, diseased liver tissue has a higher stiffness than healthy liver tissue. Accordingly, SWE imaging may be used to diagnose or monitor liver disease. Similarly, SWE imaging may be used to diagnose or monitor other organs, such as the heart. For example, in cardiac elastography, SWE imaging may be used to identify regions of the heart damaged by a myocardial infarction and/or monitor the progression of heart failure. This may allow for improved diagnosis, monitoring and/or treatment. However, the motion of the heart through the cardiac cycle as it pumps blood through the body can introduce artifacts and biases in cardiac elastography measurements. Accordingly, improved ways of acquiring cardiac elastography measurements are needed.

SUMMARY

The present application describes systems and methods for triggering the acquisition of elastography measurements based on motion data rather than EleCtrocardioGraphy (ECG) traces. Motion mode (e.g., Doppler) imaging may be used to acquire motion data to determine when a portion of a subject, such as the septum of the heart, is at rest. The use of motion data rather than ECG data to trigger the acquisition of elastography measurements may allow the acquisition of measurements at times that are not visible or associated with features of the ECG trace. This may allow measurements to be acquired when there are fewer motion artifacts and/or biases due to muscle contractions.

In accordance with at least one example described herein, an ultrasound imaging system may include an ultrasound probe configured to transmit at least one ultrasound signals and receive at least one echo signals responsive to the ultrasound signals, a motion processor configured to generate motion data from the at least one echo signals, a motion trigger generator configured to receive the motion data from the motion processor and generate a motion trigger signal based, at least in part, on the motion data, and a transmit controller configured to receive the motion trigger signal from the motion trigger generator, the transmit controller further configured to cause the ultrasound probe to acquire transmit ultrasound signals for acquiring an at least one elastography measurement based on the motion trigger signal.

In accordance with at least one example described herein, the ultrasound imaging system may further include an electrocardiography trigger generator configured to generate an electrocardiography trigger signal based on a detection of a feature in an electrocardiography trace, wherein the transmit controller is further configured, upon receipt of the electrocardiography trigger signal, to cause the ultrasound probe to acquire an elastography measurement after a delay based on the motion trigger signal.

In accordance with at least one example described herein, a method may include transmitting, with an ultrasound probe, ultrasound signals into a subject, receiving, with the ultrasound probe, echo signals from the subject responsive to the ultrasound signals, generating motion data from the echo signals, generating a motion trigger signal, based at least in part on the motion data, and transmitting, with the ultrasound probe, ultrasound signals for acquiring, with the ultrasound probe, an elastography measurement based on receipt of the motion trigger signal.

DETAILED DESCRIPTION

The following description of certain embodiments is merely exemplary in nature and is in no way intended to limit the invention or its applications or uses. In the following detailed description of embodiments of the present systems and methods, reference is made to the accompanying drawings which form a part hereof, and in which are shown by way of illustration specific embodiments in which the described systems and methods may be practiced. These embodiments are described in sufficient detail to enable those skilled in the art to practice presently disclosed systems and methods, and it is to be understood that other embodiments may be utilized and that structural and logical changes may be made without departing from the spirit and scope of the present system. While certain combinations are disclosed in the embodiments and examples described herein, it is understood that any combination of embodiments and/or examples disclosed are within the principles of the present disclosure. Moreover, for the purpose of clarity, detailed descriptions of certain features will not be discussed when they would be apparent to those with skill in the art so as not to obscure the description of the present system. The following detailed description is therefore not to be taken in a limiting sense, and the scope of the present disclosure is defined only by the appended claims.

The present technology is also described below with reference to block diagrams and/or flowchart illustrations of methods, apparatus (systems) and/or computer program products according to the present embodiments. It is understood that blocks of the block diagrams and/or flowchart illustrations, and combinations of blocks in the block diagrams and/or flowchart illustrations, may be implemented by computer executable instructions. These computer executable instructions may be provided to a processor, controller or controlling unit of a general purpose computer, special purpose computer, and/or other programmable data processing apparatus to produce a machine, such that the instructions, which execute via the processor of the computer and/or other programmable data processing apparatus, create means for implementing the functions/acts specified in the block diagrams and/or flowchart block or blocks.

The motions of the heart through each heartbeat is referred to as the cardiac cycle. The cardiac cycle consists of two major phases: systole (ejecting blood) and diastole (filling with blood). During systole, the ventricles contract, ejecting blood out of the heart to the body. Following ventricular ejection, the heart enters the diastole period. In the early diastole period, the atria fill with blood returning from the body. The heart then enters a short period of rest called diastasis. After diastasis, the atria contract, ejecting blood into the ventricles. After atrial contraction, the heart enters the next systole phase.

Figure 1:
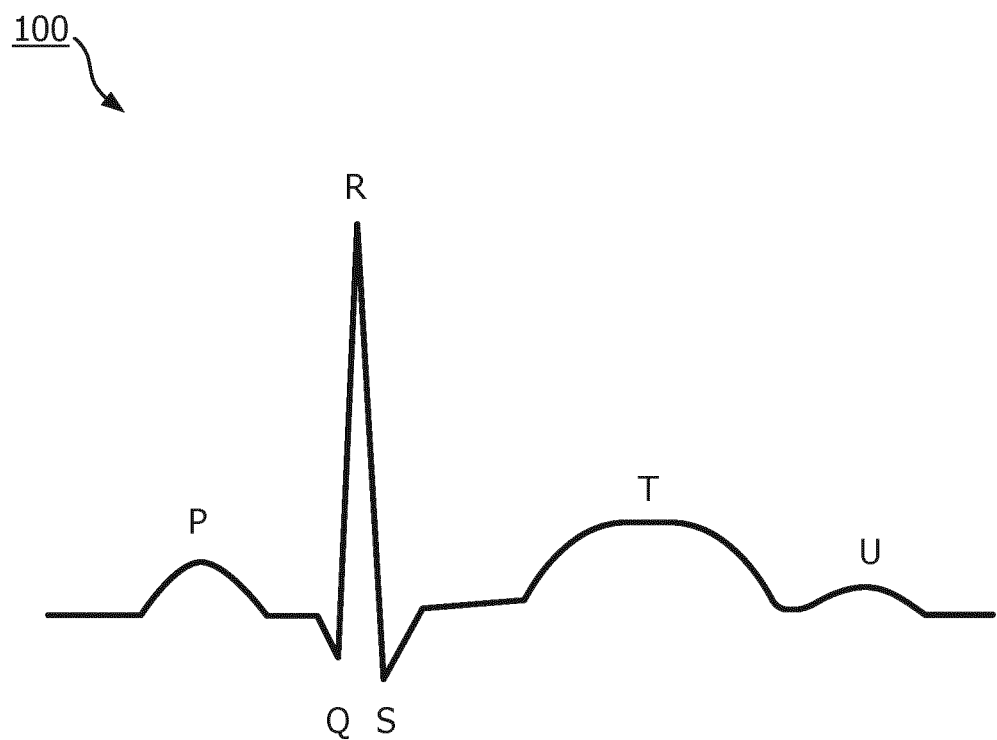
FIG. 1 is an example of an electrocardiography trace.

The phases of the cardiac cycle are associated with electrical signals generated by the heart. These electrical signals are typically monitored by ECG. During an ECG, multiple electrodes are placed on the chest and/or limbs to record electrical signals from the heart. These electrical signals are provided visually, typically on a display, as an ECG trace. An example ECG trace 100 is shown in FIG. 1. Several features of the ECG trace 100 have been assigned letters such as the P-wave, the QRS-complex, the T-wave, and the U-wave. Some features have been correlated with certain points in the cardiac cycle. For example, the P-wave is generally associated with the onset of atrial contraction and the R-wave of the QRS-complex is generally associated with the onset of ventricular contraction. The motion of the heart through the cardiac cycle can lead to motion artifacts in images and/or measurements. In electrocardiography, an ultrasound imaging system may include an ECG monitor that acquires an ECG signal from a heart of a subject being imaged. The ECG signal may be used to trigger the acquisition of images and/or used to correlate images acquired at the same point in the cardiac cycle of different heartbeats. For example, the R-wave may be used to trigger the acquisition of an image. The R-wave may be a convenient feature for use as a trigger as it is a prominent feature in the ECG trace.

ECG R-wave triggering has been used for the acquisition of elastography measurements (e.g., stiffness of cardiac tissue) via shear wave imaging. The ECG trigger ensures the elastography measurements are acquired at the same point in the cardiac cycle. Triggering at the R-wave provides measurements at the end of the diastolic period (e.g., just before the ventricles eject blood from the heart). While the R-wave triggering may ensure taking measurements at a consistent point in the cycle, cardiac stiffness measurements at end diastole are problematic. At this point in the cardiac cycle, the ventricular tissue is in motion transitioning from diastolic expansion to systolic contraction. Even if a segment of the heart is transiently immobile in this phase, the myocytes of the muscle fibers are already exerting tension, counterbalancing the effect of cardiac expansion as the ventricles prepare to contract in the next phase (e.g., systole). The tension in the muscle fibers may cause bias in elastography measurements. That is, during end diastole, SWE imaging may return stiffness values that are indicative of the tension of the muscle fibers and also the state of stretch at end-diastole, not only the health of the tissue.

Furthermore, transition from elongation to contraction does not occur simultaneously in the entire heart, which can lead to spatially dependent biases in elastography measurements. For example, a first portion of the septum may appear stiffer than a second portion due to the muscle fiber contracting in the first portion before the second portion during end diastole. These differences due to varying muscle fiber contraction states may lead to an erroneous differential measurements. Erroneous measurements may lead an incorrect diagnosis as to the health of the heart. Therefore, it is desirable to acquire elastography measurements at a point in the cardiac cycle that will reduce biases introduced by time-varying expansion, load, and contractility states of the heart.

In addition, ECG triggering for end diastole measurements are prone to timing errors. End diastole is the last heart phase when triggering on the R-wave because end diastole occurs just before the R-wave of the next cardiac cycle. Because of normal cardiac cycle length variability, precise R-wave based triggering is difficult. Even if acquisition is delayed such that it occurs after a set time after the R-wave, the delay period may need to be varied with each cardiac cycle in order to acquire measurements with the heart in the same state. Therefore, it is desirable to use a measurement acquisition trigger that is less prone to cardiac cycle variability and biases.

During electrocardiography, an ultrasound imaging system may acquire ultrasound signals via one or more modes. In B-mode (brightness mode), an ultrasound transducer array scans one or more planes through the heart for producing anatomical images. Ultrasound signals may also be used to detect and analyze motion of blood and/or tissue in the heart. This may be referred to as motion mode and/or motion imaging. One technique for acquiring motion data is acquiring ultrasound signals in Doppler mode. In Doppler mode, the ultrasound transducer array sends ultrasound pulses along one or more scan lines in the tissue to analyze motion along the scan line. The ultrasound pulses have known frequencies and the ultrasound imaging system utilizes the Doppler Effect to analyze frequency shifts in the return echoes to determine motion in the tissue at each scan line. When Doppler mode is used to analyze blood flow, it may be referred to as spectral Doppler mode, color Doppler mode, or flow mode. When Doppler mode is used to analyze movement of tissue (e.g., velocity, displacement), it is sometimes referred to as tissue Doppler mode. Doppler may also be used to determine tissue deformation and strain rates. Other motion imaging techniques including, but not limited to, cross-correlation imaging (e.g., RF signal analysis) and optical flow imaging (e.g., differential techniques, region-based matching techniques) may be used to acquire motion data.

Motion data generated by Doppler mode and/or another technique may be provided as a color-coded map where coordinates on the map correspond to a spatial location in a scanned region based on two or more dimensions (e.g., lateral location of a scan line and depth along the scan line) and the color corresponds to a magnitude of the motion (e.g., velocity, strain, displacement). This data presentation may be referred to as a color overlay. Motion data may be provided as a time-based plot. For example, a first axis of a plot may correspond to a single spatial dimension (e.g., depth along the scan line), a second axis of the plot may correspond to time, and magnitudes may be color-coded or coded in grayscale. This presentation of motion data may be referred to as an M-mode. In another example, a spatial location of motion data may be known and a first axis may correspond to magnitude and a second axis may correspond to time. This presentation is often used for presenting spectral Doppler information.

Similar to motion data, elastography measurements from SWE imaging may also be provided as a color-coded map where coordinates on the map correspond to a location in the scanned region (e.g., lateral location of a tracking line and depth along the tracking line) and the color corresponds to a magnitude of the elastography measurement (e.g., stiffness). Motion data and elastography measurements may additionally or alternatively be provided as an overlay on a B-mode image where the motion data and/or elastography measurements are overlaid on the B-mode image at locations corresponding to the locations of the measurements in the scanned region.

Figure 2:
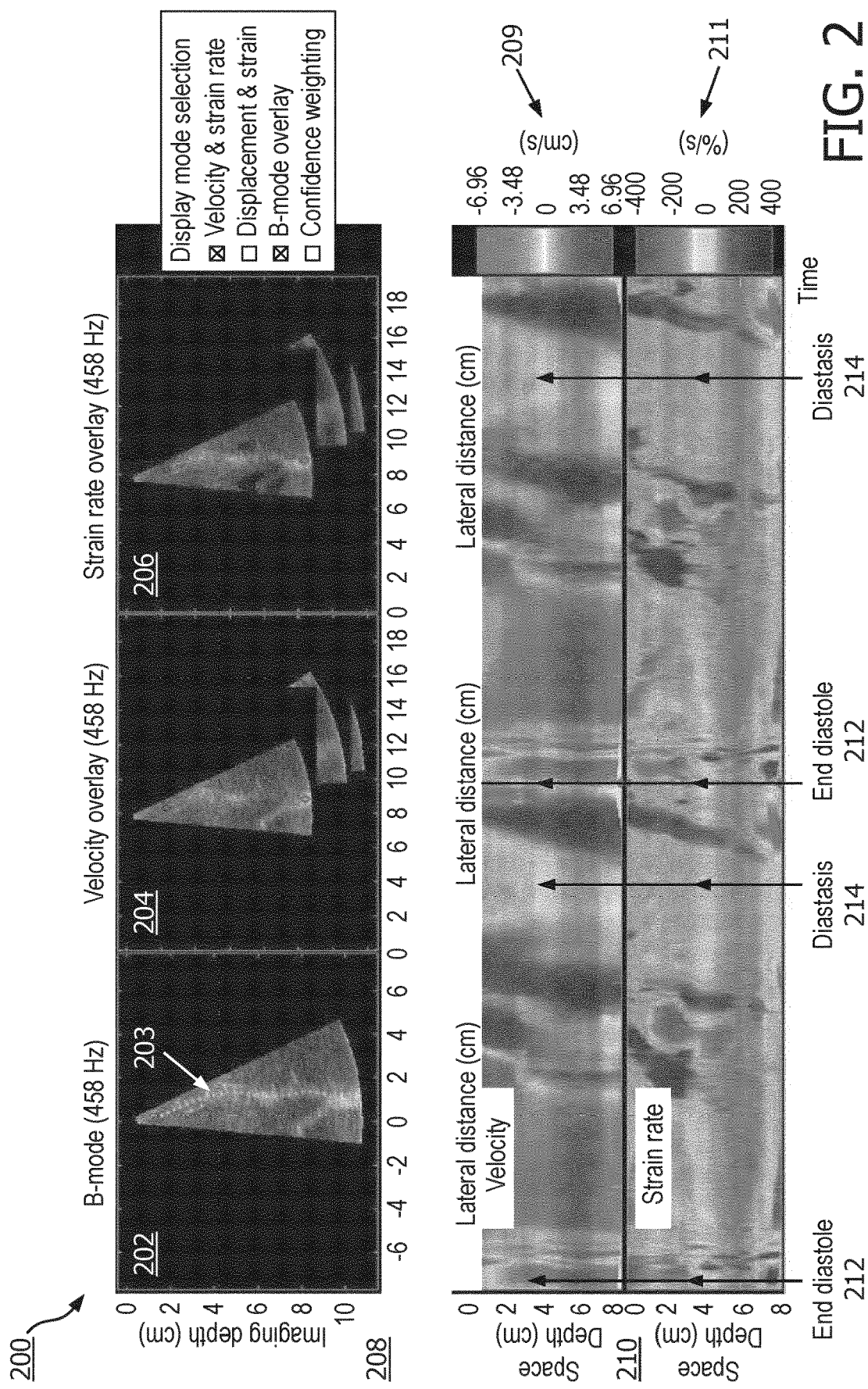
FIG. 2 is an example of a screen shot that includes displays of septal B-mode, tissue velocity, and tissue strain rate measurements in apical view, according to embodiments of the present disclosure.

FIG. 2 shows an example of a screen shot 200 produced by an ultrasound imagining system according to the present disclosure. The screen shot 200 that includes displays of B-mode, velocity, and strain rate measurements. Image 202 is a B-mode image of ultrasound imaging data for a septal myocardium in an apical 4-chamber view of a heart. An apical view shows the four chambers of the heart: left and right atria and left and right ventricles, and the septum that runs between the right and left sides of the heart. The septum is indicated by a dotted line 203.

Image 204 is the same B-mode image shown in image 202 with velocity data overlaid as a color map where different colors correspond to different velocity values. Image 206 is the same B-mode image shown in image 202 with strain rate data overlaid as a color map where different colors correspond to different strain rate values.

Plot 208 is an alternative visualization of velocity data. The vertical axis corresponds to depth along a single scan line which approximates the line of the septum (see the dotted line 203 in image 202). The horizontal axis corresponds to time. The different colors in plot 208 indicate different velocity values as indicated by legend 209. Plot 210 is an alternative visualization of strain rate data. The vertical axis corresponds to depth along a single scan line which approximates the line of the septum. The horizontal axis corresponds to time. The different colors in plot 210 indicate different strain rate values as indicated by legend 211. The time axis shows the end diastole 212 and diastasis 214.

In addition to providing an example of how B-mode and different types of motion data may be provided on a display, FIG. 2 illustrates the difficulties of acquiring elastography measurements at end diastole 212. As shown at end diastole 212 on the velocity data presented in plot 208, there is significant motion and acceleration occurring at end-diastole. Similarly, at end diastole 212, the strain rate data presented in plot 210 show significant contraction and extension of tissue. Furthermore, as seen in the velocity data in plot 208 and strain rate data in plot 210, tissue motion and strain rates at end-diastole are spatially dependent. That is, the extent of tissue motion and contraction vary with location along the scan line 203 of the septum. Thus, elastography measurements taken at end-diastole may be inaccurate due to variabilities in velocity and strain rates. However the velocity and strain rate show little change spatially during the diastasis period; assuming, that for this example, the septum of the heart is healthy uniform tissue.

Figure 3:
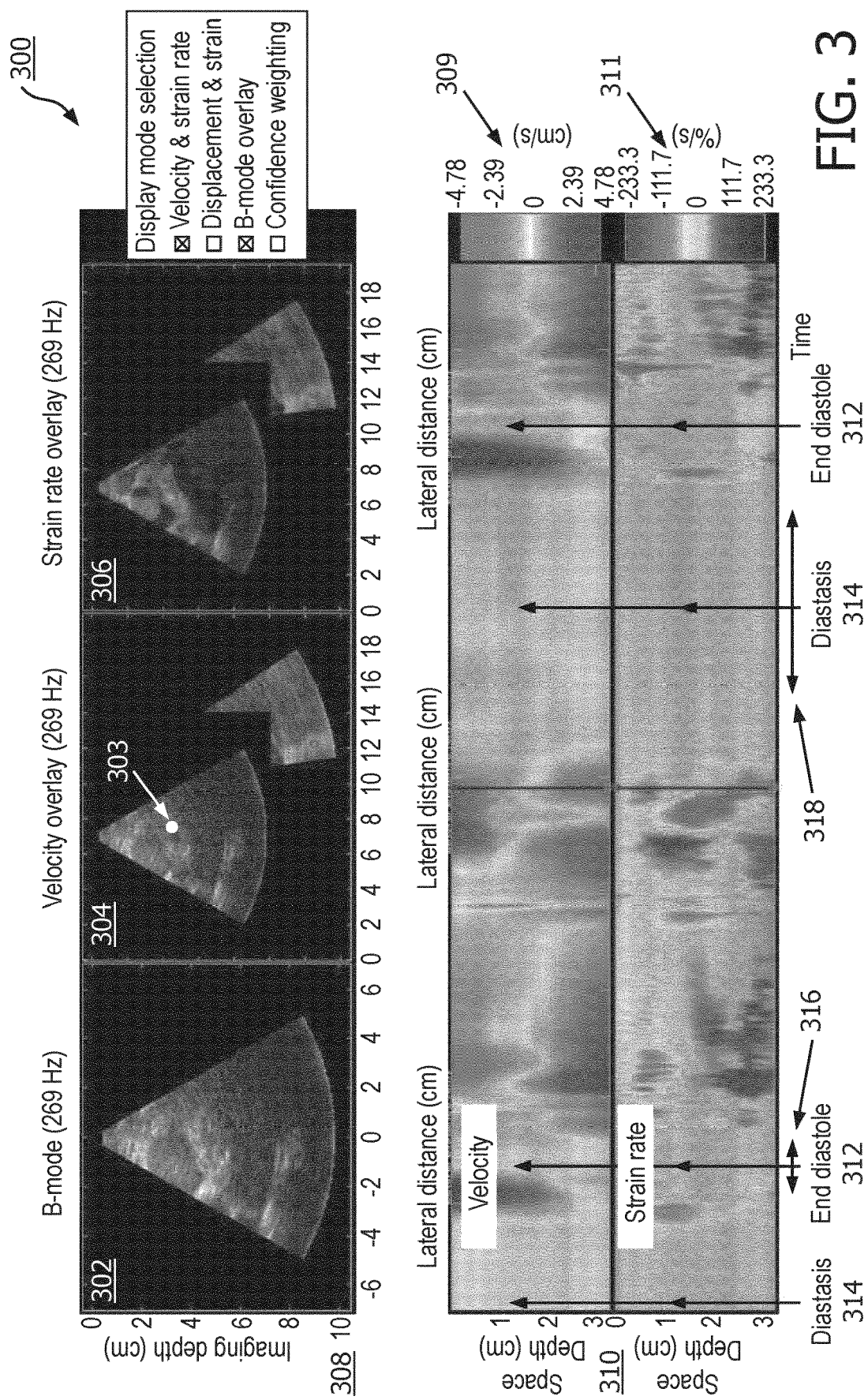
FIG. 3 is a further example of ultrasound imaging system screen shot that includes displays of septal B-mode, tissue velocity, and tissue strain rate measurements in parasternal long-axis view, according to embodiments of the present disclosure.

FIG. 3 shows another example of ultrasound imaging system screen shot 300 that includes displays of B-mode, velocity, and strain rate measurements. Image 302 is a B-mode image of ultrasound imaging data for a septal myocardium in a parasternal long-axis view of the septal curve in a heart. Parasternal long-axis view shows the septum oriented horizontally between the left and right sides of the heart. Image 304 is the same B-mode image shown in image 302 with velocity data overlaid as a color map where different colors correspond to different velocity values. A dot 303 is located at a point along the septum. Image 306 is the same B-mode image shown in image 302 with strain rate data overlaid as a color map where different colors correspond to different strain rate values.

Plot 308 is an alternative visualization of velocity data. The vertical axis corresponds to depth along a scan line through the septum at the location indicated by dot 303. The horizontal axis corresponds to time. The different colors in plot 308 indicate different velocity values as indicated by legend 309. Plot 310 is an alternative visualization of strain rate data. The vertical axis corresponds to depth along a scan line through the septum at the location indicated by dot 303. The horizontal axis corresponds to time. The different colors in plot 310 indicate different strain rate values as indicated by legend 311.

Similar to FIG. 2, FIG. 3 illustrates the difficulties of acquiring elastography measurements at end diastole. As shown at end diastole 312 on the velocity data presented in plot 308, there is significant motion and acceleration occurring at end-diastole. There is only a very narrow time window, indicated by double-ended arrow 316, where velocity values appear at a minimum on plot 308. Similarly, at end diastole 312, the strain rate data presented in plot 310 show significant contraction and extension of tissue on either side of the narrow time window around end diastole 312. This brief minimum of velocity/strain rate occurs slightly before the R wave. There is significant motion and strain rate at the peak of the R wave. Furthermore, similar to the velocity data in plot 208 and strain rate data 210 in FIG. 2 taken along a different scan line of the septum, the velocity data in plot 308 and strain rate data in plot 310 illustrate that tissue motion and strain rates at end-diastole are spatially dependent. Thus, as previously noted, elastography measurements taken at end-diastole may be inaccurate due to variabilities in velocity and strain rates.

To reduce inaccuracies, it is preferable to acquire SWE measurements (e.g., elastography measurements) when motion and strain rates are minimal. Referring to FIG. 3 for example, the inventors have observed that at diastasis 314, the entire heart is relatively quiescent for a relatively long time compared to end-diastole 314, as indicated by double-ended arrow 318 in FIG. 3. The velocity data in plot 308 at diastasis 314 shows far less tissue motion that is less spatially dependent. The strain rate data in plot 310 also shows lower levels of strain that is less spatially dependent at diastasis 314 compared to end diastole 312. ECG-trigger based systems may not be able to take advantage of the observed quiescent state of the heart at diastasis as this state is not visible on an ECG trace or associated with a feature of the ECG trace. Accordingly, the inventors have conceived of an ultrasound SWE system, which employs an alternative method of triggering for the acquisition of elastography measurements. In accordance with the principles of the present invention, motion data from Doppler imaging may be used to trigger shear wave imaging to acquire elastography measurements. Motion data may include tissue displacement, tissue velocity, acceleration deformation, strain, strain rate, and/or blood flow data. The use of a motion-based trigger may allow a user to acquire elastography measurements at portions of the cardiac cycle, such as mid-diastole (e.g., diastasis), that cannot be detected by an ECG trace. This may allow for the acquisition of elastography measurements that are more accurate, less biased, and/or more reproducible.

Figure 4:
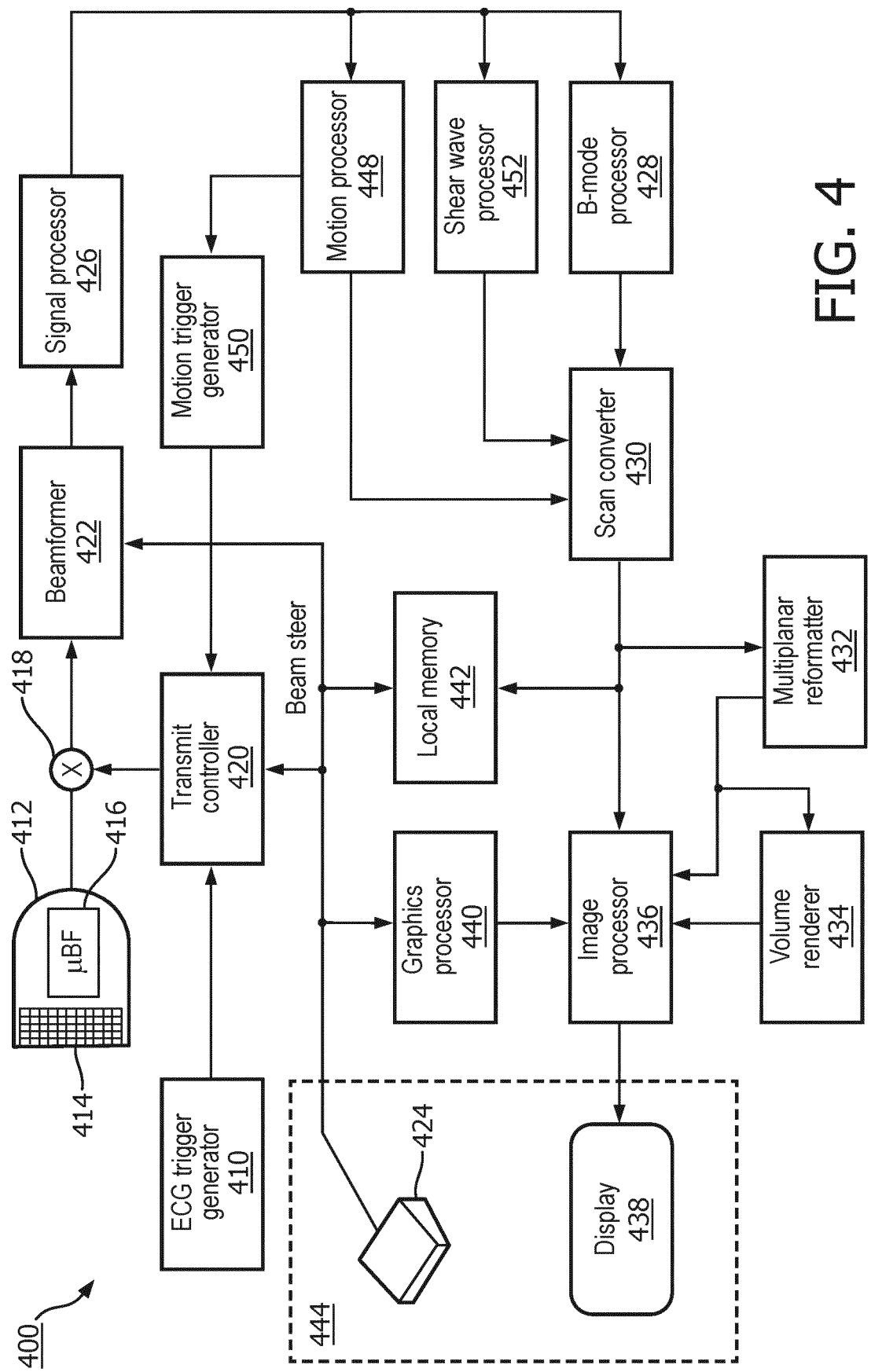
FIG. 4 is a block diagram of an ultrasound imaging system according to embodiments of the present disclosure.

FIG. 4 shows a bock diagram of an ultrasound imaging system 400 in accordance with embodiments of the present disclosure. The ultrasound imaging system 400 may include components that allow the ultrasound imaging system 400 to perform B-mode imaging, M-mode imaging, spectral imaging, and/or shear wave imaging (e.g., elastography). The ultrasound imaging device may include processing components (e.g., one or more beamformers, signal processor, etc.) communicatively coupled to an ultrasound probe operable to transmit ultrasound and receive echoes from a subject. The components and the arrangement thereof shown in FIG. 4 are merely illustrative, and other variations, including eliminating components, combining components, rearranging components, and substituting components are all contemplated.

As shown in FIG. 4, the ultrasonic imaging system 400 may include an ultrasound probe 412 includes a transducer array 414 for transmitting ultrasound signals (e.g., ultrasonic beams) toward a target region of a subject and receiving echo signals responsive to the ultrasound signals. A variety of transducer arrays are known in the art, e.g., linear arrays, convex arrays or phased arrays. The transducer array 414, for example, can include a two dimensional array (as shown) of transducer elements capable of scanning in both elevation and azimuth dimensions for 2D and/or 3D imaging. The transducer array 414 may be capable of transmitting ultrasound signals and receiving echo signals for different imaging modes (e.g., B-mode imaging, Doppler imaging, and/or shear wave imaging). In some embodiments, ultrasound probe 412 may include multiple transducer arrays 414 configured for use in different imaging modes.

In some embodiments, the transducer array 414 may be coupled to a microbeam former 416 in the probe 412, which controls transmission and reception of signals by groups of transducer elements in the transducer array 414. In this example, the microbeamformer is coupled by a probe cable to a transmit/receive (T/R) switch 418, which switches between transmission and reception and protects the main beamformer 422 from high energy transmit signals. In some embodiments, the probe may be coupled wirelessly to the signal and image processing components. Typically, the signal and image processing components are located in an ultrasound system base. In some embodiments, the T/R switch 418 and other elements in the system can be included in the transducer probe 412 rather than in the separate ultrasound system base.

The transmission of ultrasonic signals from the transducer array 414 under control of the microbeamformer 416 is directed by the transmit controller 420 coupled to the T/R switch 418 and the beamformer 422. The transmit controller 420 may control when ultrasonic signals are transmitted and/or what type of ultrasonic signals are transmitted (e.g., beams suitable for B-mode, shear wave, and/or Doppler). The transmit controller 420 may control the direction in which beams are steered. Beams may be steered straight ahead from (orthogonal to) the transducer array, or at different angles for a wider field of view. The transmit controller 420 may receive input from the user's operation of control panel 424 of a user interface 444, an ECG trigger generator 410, and/or a motion trigger generator 450. These inputs may determine the steering, timing, and/or type of transmission of ultrasonic signals directed by the transmit controller 420.

The received partially beamformed signals produced by the microbeamformer 416 are coupled to a main beamformer 422 where partially beamformed signals from individual patches of transducer elements are combined into a fully beamformed signal. In some embodiments, microbeamformer 416 is omitted, and the transducer array 414 is under the control of the beamformer 422. The beamformed signals are coupled to a signal processor 426. The signal processor 426 can process the received echo signals in various ways, such as bandpass filtering, decimation, I and Q component separation, and harmonic signal separation. The signal processor 426 may also perform additional signal enhancement such as speckle reduction, signal compounding, and noise elimination.

The processed signals are coupled to a B-mode processor 428, which can employ amplitude detection for the imaging of structures in the body. The signals produced by the B-mode processor 428 are coupled to a scan converter 430 and a multiplanar reformatter 432. The scan converter 430 arranges the echo signals in the spatial relationship from which they were received in a desired image format. For instance, the scan converter 430 may arrange the echo signal into a two dimensional (2D) sector-shaped format, or a pyramidal three dimensional (3D) image. The multiplanar reformatter 432 can convert echoes, which are received from points in a common plane in a volumetric region of the body into an ultrasonic image of that plane, as described in U.S. Pat. No. 6,443,896 (Detmer). A volume renderer 434 converts the echo signals of a 3D data set into a projected 3D image as viewed from a given reference point, e.g., as described in U.S. Pat. No. 6,530,885 (Entrekin et al.) The 2D or 3D images are coupled from the scan converter 430, multiplanar reformatter 432, and volume renderer 434 to an image processor 436 for further enhancement, buffering and temporary storage for display on an image display 438. A graphics processor 440 can generate graphic overlays for display with the ultrasound images. These graphic overlays can contain, e.g., standard identifying information such as patient name, date and time of the image, imaging parameters, and the like. For these purposes the graphics processor 440 receives input from the user interface 444, such as a typed patient name. The user interface 444 can also be coupled to the multiplanar reformatter 432 for selection and control of a display of multiple multiplanar reformatted (MPR) images.

The processed signals may also be provided to a shear wave processor 452. Shear wave velocity and elastography measurements (e.g., tissue stiffness) may be estimated by the shear wave processor 452, which may be configured to implement any currently known or later developed shear wave elastography techniques. The elastography measurements may be provided to the scan converter 430 which may correlate the elastography measurements with corresponding locations in the B-mode image. Correlating the elastography measurements with the B-mode image may allow the elastography measurements to be provided as a graphical overlay on the B-mode image.

The processed signals may further be provided to a motion processor 448. The motion processor 448 may be capable of performing tissue motion imaging, Doppler spectral imaging, and/or other motion-based imaging (e.g., strain rate). In some embodiments, the motion processor 448 may include separate processors for different motion-based imaging. The motion processor 448 may be configured to determine motion data (e.g., tissue motion, fluid flow) by implementing any currently known or later developed motion imaging techniques, such as Doppler. The motion processor 448 may provide motion data to the scan converter 430 which may correlate the motion data with corresponding locations in the B-mode image. Correlating the motion data with the B-mode image may allow the motion data to be provided as a graphical overlay on the B-mode image. For example, the overlay images 204 and 304 shown in FIGS. 2 and 3, respectively.

The motion data and/or elastography measurements may be provided to image processor 436 via scan converter 430 to generate graphical representations of the motion data and/or elastography measurements. Examples include, but are not limited to, color-maps and time-dependent plots. For example, the plots 208 and 310 shown in FIGS. 2 and 3, respectively.

As shown in FIG. 4, the system 400 may include a motion trigger generator 450 configured to generate a motion-based trigger signal. The motion trigger generator 450 may be implemented by a controller, a processor, or an application specific circuit. Motion data generated by the motion processor 448 may be provided to the motion trigger generator 450, which may analyze the motion data to determine when a portion of a subject (e.g., blood flow in a vessel, muscle tissue) being scanned is at rest. For example, the trigger generator may process the motion data to determine whether one or more motion related parameters of the motion data (e.g., velocity, acceleration, and/or strain rate) are below a threshold value. The threshold value may be dependent upon the type of motion related parameter being evaluated as well as the type of tissue being evaluated. For example, blood flow velocities may be higher than tissue movement velocities, e.g., tissue motion is on the order of 10-12 cm/s and blood motion at the mitral valve is on the order of 50-6 cm/s.

In some embodiments, if the motion related parameter is below the threshold value for a given period of time. For example, for cardiac elastography, motion data may indicate the heart is at rest when the velocity falls below 1 cm/sec for at least 70 msec. In another example, the motion data may indicate the heart is at rest when the acceleration falls below 1 cm/sec$^2$ or 10 cm/sec$^2$ for at least 50 msec. In some embodiments, multiple motion related parameters may be used. For example, the motion data may indicate the heart is at rest when the velocity falls below 1 cm/sec and acceleration falls below 1 cm/sec or 10 cm/sec. In another example, the motion data may indicate the heart is at rest when the velocity falls below 1 cm/sec and the strain rate falls below 10%/sec. In some embodiments, a time period of the motion parameters may be used. For example, when the conditions described above persist for more than 50 msec. These examples are for illustrative purposes and the motion trigger generator 450 determination of when the portion of the subject is at rest is not limited to the examples described. The threshold value may be pre-set by the ultrasound imaging system 400 or it may be set by a user via the user interface 444.

When the motion trigger generator 450 determines the tissue is at rest, the motion trigger generator 450 may send a motion trigger signal to the transmit controller 420. The motion trigger signal may cause the transmit controller 420 to cause the transducer array 414 to perform SWE imaging for acquiring elastography measurements. The elastography measurements need not be acquired at the same location where the motion data was acquired. For example, motion data may be acquired at a septum of a heart, and elastography measurements may be taken at the left ventricle wall of the heart. In another example, motion data may be acquired for blood flow at the mitral valve of the heart, and elastography measurements may be acquired for the entire heart.

The system may include an ECG trigger generator 410. The ECG trigger generator 410 may be implemented as a controller, a processor, or a suitable circuit. The ECG trigger generator 410 may receive an ECG signal from a subject being scanned by system 400. The ECG trigger generator 410 may analyze the ECG signal to detect a feature in an ECG trace (e.g., an R-wave of a QRS complex). The ECG trigger generator 410 may send an ECG trigger signal to the transmit controller 420. In some embodiments, the ECG trigger signal may cause the transmit controller 420 to cause the transducer array 414 to acquire ultrasound signals (e.g., B-mode, Doppler, SWE). In some embodiments, there may be a delay between the ECG trigger signal and the transmit controller 420 causing the transducer array 414 to acquire ultrasound signals. The delay may be pre-set in system 400, programmed by a user via the user interface 444, and/or based on the motion trigger signal. In some embodiments, the ECG trigger generator 410 may be used to synchronize acquired images. For example, the ECG trigger signal may allow images acquired over one or more cardiac cycles to be arranged based, at least in part, on when in the cardiac cycle the images were acquired.

In some embodiments, the ECG trigger signal may be used by the transmit controller 420 to synchronize acquired B-mode images while the motion trigger signal may be used by the transmit controller 420 to acquire SWE images for elastography measurements. Using the motion trigger signal to control the acquisition of cardiac elastography measurements by the transmit controller 420 may allow the measurements to be acquired during mid-diastole (i.e., diastasis) when the heart is at rest. The measurements may be more accurate and less prone to motion errors and biases due to muscle contractions.

In some embodiments, the motion trigger signal may be used by the transmit controller 420 to program a delay between the ECG trigger signal and the transmission of ultrasound signals (e.g., B-mode, Doppler, and/or SWE). In some embodiments, the transmit controller 420 may automatically program the delay based on the motion trigger signal. In other embodiments, a user may view motion data on a display (e.g., display 438) and enter a delay via the user interface 444. Data from the motion trigger signal may be used to assist the user in inputting the delay. While using the motion data to apply a delay to the ECG trigger signal may cause cardiac elastography measurements to be vulnerable to natural variations in the timing of the cardiac cycle, basing the delay on motion data allows elastography measurements to be acquired ad mid-diastole (i.e., diastasis), which lasts for a longer period of time than end-diastole. Furthermore, using motion data to generate a delay to the ECG trigger signal generated by ECG trigger generator 410 may be easier to implement in some existing ultrasound imaging systems than acquisition based solely on a motion-based trigger (e.g., motion trigger generator 450).

The system 400 may include local memory 442. Local memory 442 may be implemented as any suitable non-transitory computer readable medium (e.g., flash drive, disk drive). Local memory 442 may store data generated by the system 400 including B-mode images, elastography measurements, motion data, executable instructions, inputs provided by a user via the user interface 444, or any other information necessary for the operation of the system 400.

As mentioned previously system 400 includes user interface 444. User interface 444 may include display 438 and control panel 424. The display 438 may include a display device implemented using a variety of known display technologies, such as LCD, LED, OLED, or plasma display technology. In some embodiments, display 438 may comprise multiple displays. The control panel 424 may be configured to receive user inputs. The control panel 424 may include one or more hard controls (e.g., buttons, knobs, dials, encoders, mouse, trackball or others). In some embodiments, the control panel 424 may additionally or alternatively include soft controls (e.g., GUI control elements or simply, GUI controls) provided on a touch sensitive display. In some embodiments, display 438 may be a touch sensitive display that includes one or more soft controls of the control panel 424.

In some embodiments, various components shown in FIG. 4 may be combined. For instance, image processor 436 and graphics processor 440 may be implemented as a single processor. In some embodiments, various components shown in FIG. 4 may be implemented as separate components. For example, signal processor 426 may be implemented as separate signal processors for each imaging mode (e.g., B-mode, motion, and shear wave). In some embodiments, one or more of the various processors shown in FIG. 4 may be implemented by general purpose processors and/or microprocessors configured to perform the specified tasks. In some embodiments, one or more of the various processors may be implemented as application specific circuits. In some embodiments, one or more of the various processors (e.g., image processor 436) may be implemented with one or more graphical processing units (GPU).

Figure 9:
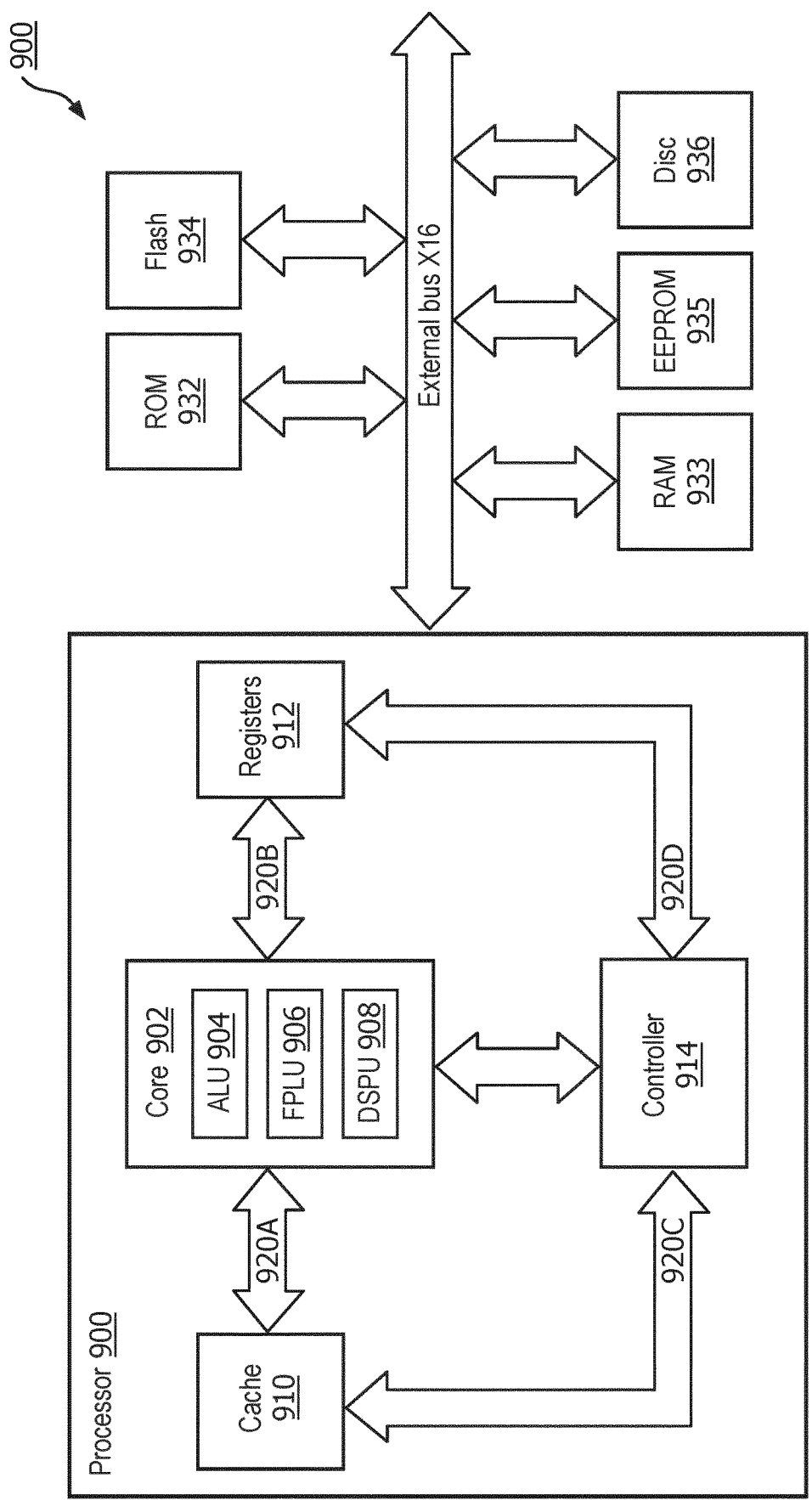
FIG. 9 is a block diagram illustrating an example processor according to embodiments of the disclosure.

FIG. 9 is a block diagram illustrating an example processor 900 according to embodiments of the disclosure. Processor 900 may be used to implement one or more processors described herein, for example, signal processor 426, motion processor 448, shear wave processor 452, B-mode processor 428, graphics processor 440, and/or image processor 436 shown in FIG. 4. In some examples, processor 900 may be used to implement or implement a portion of one or more components described herein, for example, motion trigger generator 450, ECG trigger generator 410, scan converter 430, multiplanar reformatter 432, and/or volume renderer 434 shown in FIG. 4. Processor 900 may be any suitable processor type including, but not limited to, a microprocessor, a microcontroller, a Digital Signal Processor (DSP), a Field Programmable Gate Array (FPGA) where the FPGA has been programmed to form a processor, a Graphical Processing Unit (GPU), an Application Specific Integrated Circuit (ASIC) where the ASIC has been designed to form a processor, or a portion of custom integrated circuit or a combination thereof.

The processor 900 may include one or more cores 902 (one shown). The core 902 may include one or more arithmetic logic units (ALU) 904 (one shown). In some embodiments, the core 902 may include one or more Floating Point Logic Unit (FPLU) 906 (one shown) and/or one or more Digital Signal Processing Unit (DSPU) 908 (one shown) in addition to or instead of the one or more ALU 904.

The processor 900 may include one or more registers 912 communicatively coupled to the core 902. The registers 912 may be implemented using dedicated logic gate circuits (e.g., flip-flops) and/or any suitable memory technology. In some embodiments the registers 912 may be implemented using static memory. The register may provide data, instructions and addresses to the core 902.

In some embodiments, processor 900 may include one or more levels of cache memory 910 communicatively coupled to the core 902. The cache memory 910 may provide computer-readable instructions to the core 902 for execution. The cache memory 910 may provide data for processing by the core 902. In some embodiments, the computer-readable instructions may be provided to the cache memory 910 by a local memory, for example, local memory attached to the external bus 916. The cache memory 910 may be implemented with any suitable cache memory type, for example, Metal-Oxide Semiconductor (MOS) memory such as Static Random Access Memory (SRAM), Dynamic Random Access Memory (DRAM), and/or any other suitable memory technology.

The processor 900 may include a controller 914, which may control input to the processor 900 from other processors and/or components included in a system (e.g., beamformer 422 shown in FIG. 4) and/or outputs from the processor 900 to other processors and/or components included in the system (e.g., signal processor 426 shown in FIG. 4). Controller 914 may control the data paths in the ALU 904, FPLU 906 and/or DSPU 908. Controller 914 may be implemented as one or more state machines, data paths and/or dedicated control logic. The gates of controller 914 may be implemented as standalone gates, FPGA, ASIC or any other suitable technology.

The registers 912 and the cache 910 may communicate with controller 914 and core 902 via internal connections 920A, 920B, 920C and 920D. Internal connections may be implemented as a bus, multiplexor, crossbar switch, and/or any other suitable connection technology.

Inputs and outputs for the processor 900 may be provided via a bus 916, which may include one or more conductive lines. The bus 916 may be communicatively coupled to one or more components of processor 900, for example the controller 914, cache 910, and/or register 912. The bus 916 may be coupled to one or more components of the system, such as shear wave processor 452 and signal processor 426 mentioned previously. Bus 916 may be implemented as a bus, multiplexor, crossbar switch, and/or any other suitable connection technology The bus 916 may be coupled to one or more external memories. The external memories may include Read Only Memory (ROM) 932. ROM 932 may be a masked ROM, Electronically Programmable Read Only Memory (EPROM) 935 or any other suitable technology. The external memory may include Random Access Memory (RAM) 933. RAM 933 may be a static RAM, battery backed up static RAM, DRAM, SRAM or any other suitable technology. The external memory may include Electrically Erasable Programmable Read Only Memory (EEPROM) 935. The external memory may include Flash memory 934. The External memory may include a magnetic storage device such as disc 936. In some embodiments, the external memories may be included in a system, such as ultrasound imaging system 400 shown in FIG. 4.

Returning to FIG. 4, as described herein, in some embodiments, an ultrasound imaging system may include an ultrasound probe (e.g., probe 412) configured to transmit ultrasound signals and receive echo signals responsive to the ultrasound signals to scan a subject, a motion processor (e.g., motion processor 448) configured to generate motion data from the echo signals, a motion trigger (e.g., motion trigger generator 450) configured to receive the motion data and generate a motion trigger signal based, at least in part, on the motion data, and a transmit controller (e.g., transmit controller 420) configured to cause the ultrasound probe to transmit ultrasound signals for acquiring an elastography measurement based on the motion trigger signal.

As described herein, in some embodiments, an ultrasound imaging system may include an ultrasound probe (e.g., probe 412) configured to transmit ultrasound signals and receive echo signals responsive to the ultrasound signals, an electrocardiography trigger (e.g., ECG trigger generator 410) configured to receive an electrocardiography trace and generate an electrocardiography trigger signal based on a detection of a feature in the electrocardiography trace, a motion processor (e.g., motion processor 448) configured to generate motion data from the echo signals, a motion trigger generator (e.g., motion trigger generator 450) configured to receive the motion data and generate a motion trigger signal based, at least in part, on the motion data, a transmit controller (e.g., transmit controller 420) configured to receive the electrocardiography trigger signal and the motion trigger signal, the transmit controller further configured, upon receipt of the electrocardiography trigger to cause the ultrasound probe to transmit ultrasound signals for acquiring an elastography measurement after a delay based on the motion trigger signal.

Figure 5:
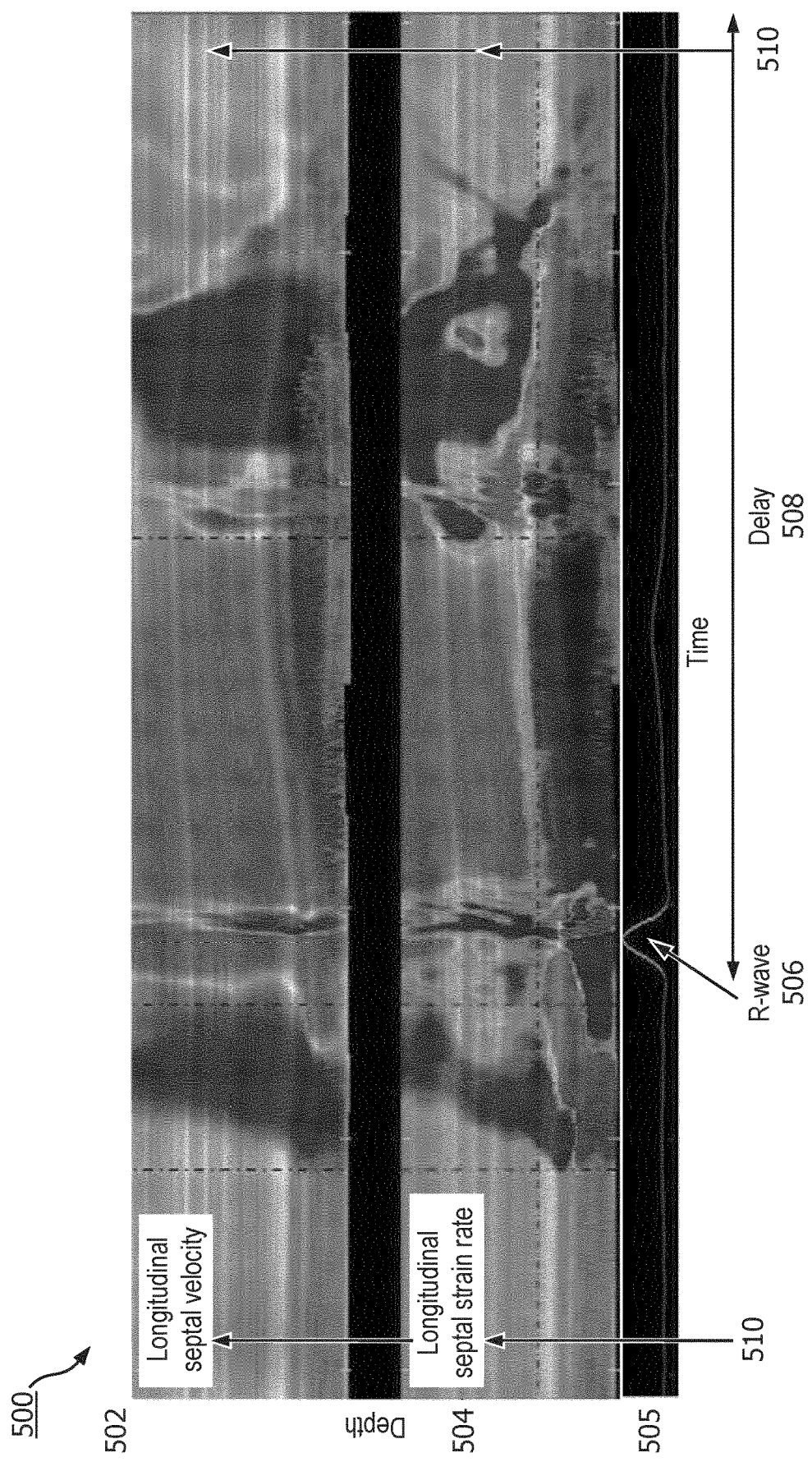
FIG. 5 illustrates an example of determining a motion trigger and a delay based on tissue velocity and strain rate M-mode data according to embodiments of the present disclosure.
Figure 6:
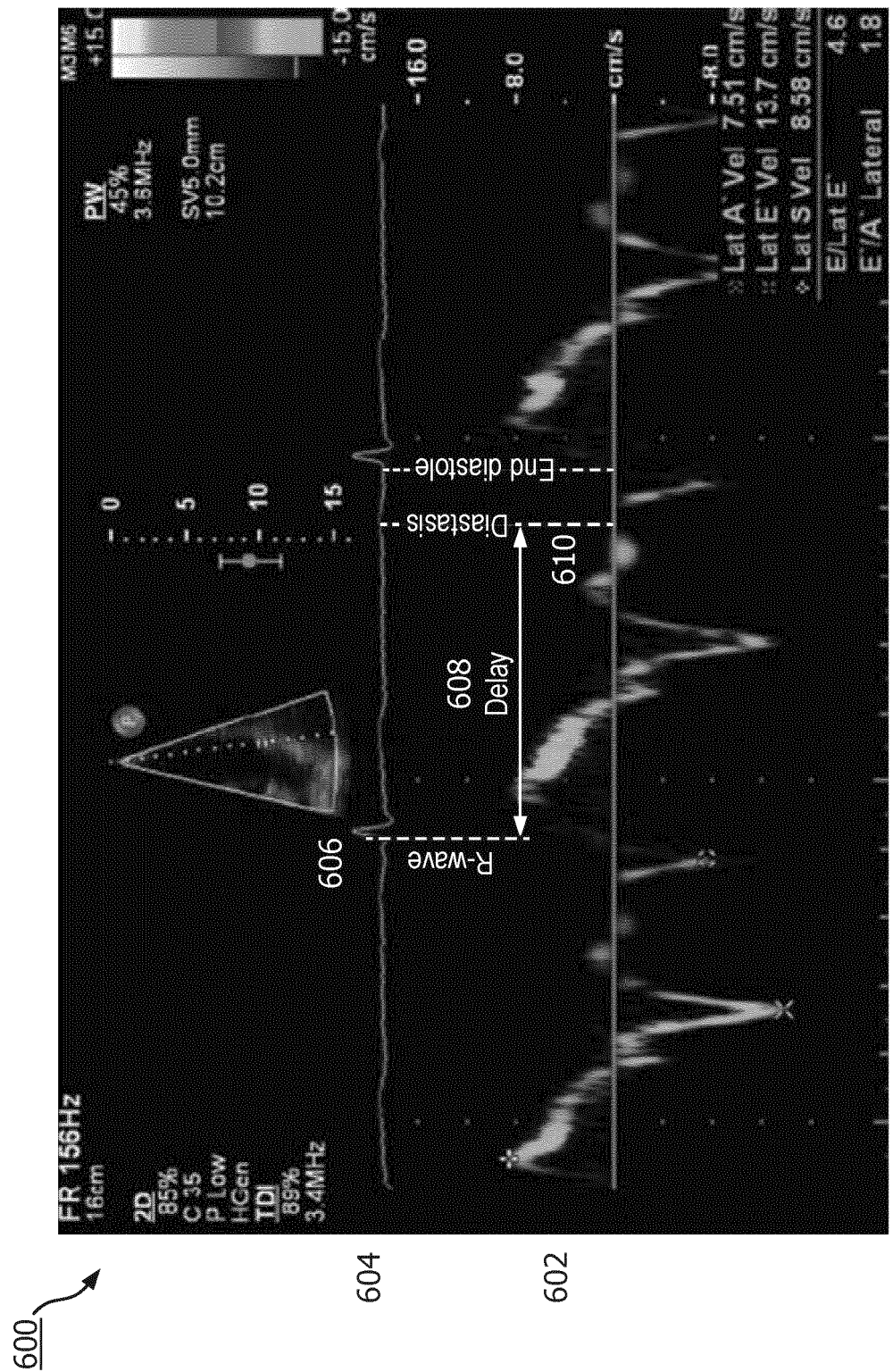
FIG. 6 illustrates an example of determining a motion trigger and a delay based on spectral tissue Doppler data according to embodiments of the present disclosure.
Figure 7:
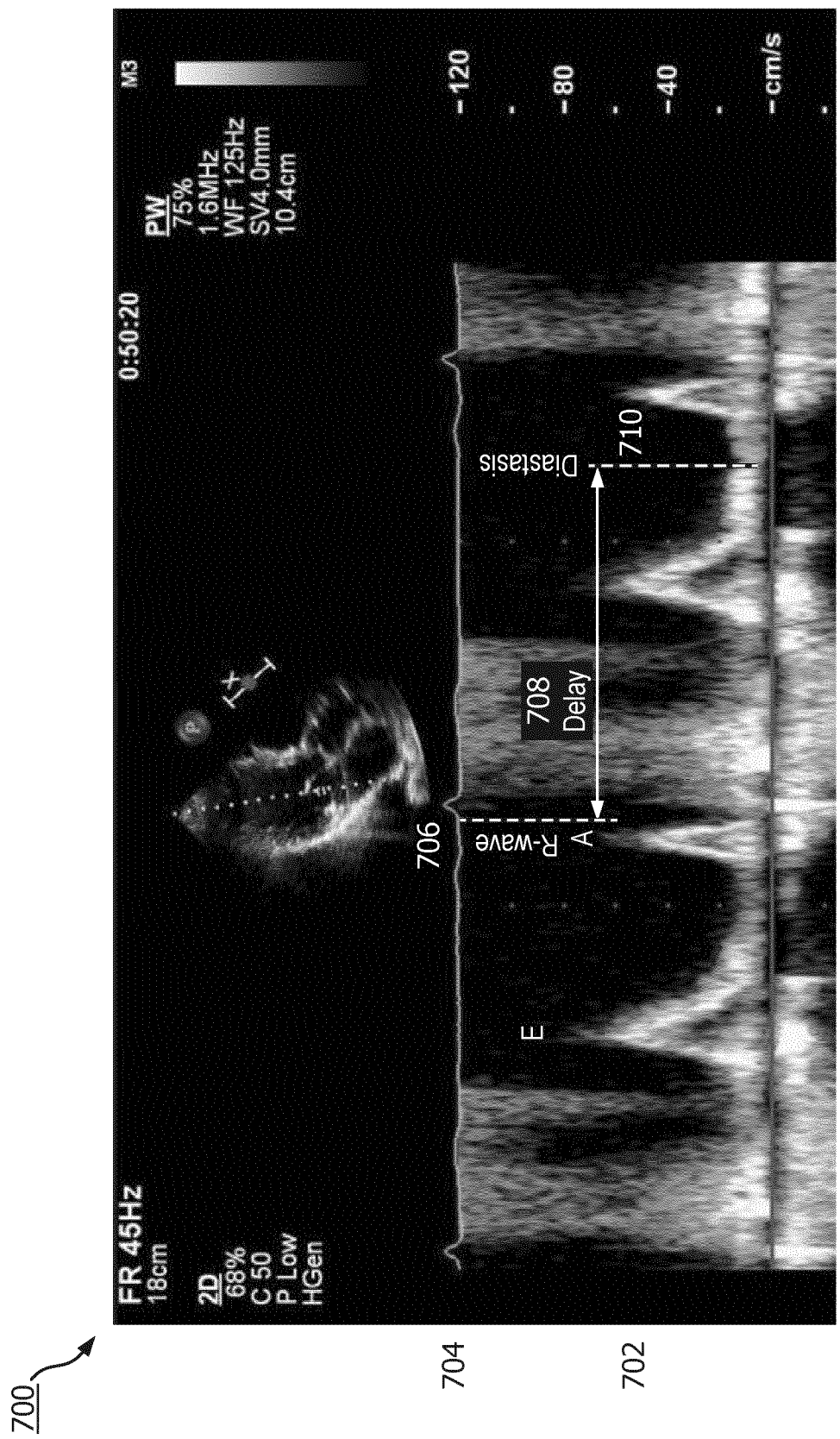
FIG. 7 illustrates an example of determining a motion trigger and a delay based on Doppler flow data according to embodiments of the present disclosure.

With reference to FIGS. 5-7, certain examples consistent with the embodiments presented herein will be described. The examples provided are for illustrative purposes and embodiments of the disclosure are not limited to the examples described.

FIG. 5 illustrates an example of determining motion trigger and a delay based on M-mode data 500 according to embodiments of the present disclosure. In the example shown in FIG. 5, the M-mode data includes plot 502 of velocity data. The vertical axis indicates a depth along a scan line through a septum of a heart and the horizontal axis indicates a time of acquisition. The different colors of plot 502 indicate different velocity magnitudes. The M-mode data further includes plot 504 of strain rate data. The vertical axis indicates a depth along a scan line through the septum of the heart and the horizontal axis indicates the time of acquisition. The different colors of plot 502 indicate different strain rate magnitudes. Below the M-mode data is an ECG trace 505 plotted over time. As shown in FIG. 5, after the R-wave 506 appears on the ECG trace 505, velocity and strain rate magnitudes dramatically increase as the heart enters systole. After a delay 508 from the R-wave 506, the heart enters diastasis 510, where velocity and strain rates are at a minimum.

In an ultrasound imaging system where elastography measurements are acquired based solely on a motion-based trigger, such as motion trigger generator 450, the velocity data and/or strain rate data shown in plots 502 and 504 may be analyzed to determine when the heart is at rest. The determination may be based on when the velocity and/or strain rate falls below a threshold value. Once the heart is determined to be at rest, a motion trigger signal is sent to a transmit controller, which will then cause an ultrasound transducer to acquire elastography measurements of the heart.

In an ultrasound imaging system where elastography measurements are acquired based on a modified ECG trigger signal, the velocity data and/or strain rate data shown in plots 502 and 504 may be analyzed to determine when the heart is at rest, similar to the method described in the previous paragraph. Once the heart is determined to be at rest, the delay 508 between the R-wave 506 and the resting state (e.g., diastasis 510) is determined. The determination may be performed by the motion trigger generator or the transmit controller may calculate the delay 508 based on the signal provided by the motion trigger generator. When the transmit controller receives an ECG trigger signal (e.g., from ECG trigger generator 410), the transmit controller will wait to acquire elastography measurements until the delay 508 has passed.

FIG. 6 illustrates an example of determining a motion trigger and a delay based on spectral tissue Doppler data according to embodiments of the present disclosure. In the example screen shot 600 shown in FIG. 6, the spectral tissue Doppler data includes plot 602 of velocity data acquired at a mitral annulus of a heart. The vertical axis indicates a velocity magnitude (cm/s) and the horizontal axis indicates time(s). Above the spectral tissue Doppler data is an ECG trace 604 plotted over time. As shown in FIG. 6, after the R-wave 606 appears on the ECG trace 604, velocity magnitudes dramatically increase as the heart enters systole. After a delay 608 from the R-wave 606, the heart enters diastasis 610, where velocity values are at a minimum.

In an ultrasound imaging system where elastography measurements are acquired based solely on a motion-based trigger signal generated by a trigger signal generator, such as motion trigger generator 450, the velocity data shown in plot 602 may be analyzed to determine when the heart is at rest. The determination may be based on when the velocity and/or a slope of the velocity curve (e.g., acceleration) falls below a threshold value. Once the heart is determined to be at rest, a motion trigger signal is sent to a transmit controller, which will then cause an ultrasound transducer to acquire elastography measurements of the heart.

In an ultrasound imaging system where elastography measurements are acquired based on a modified ECG trigger signal, the velocity data shown in plot 602 may be analyzed to determine when the heart is at rest, similar to the method described in the previous paragraph. Once the heart is determined to be at rest, the delay 608 between the R-wave 606 and the resting state (e.g., diastasis 610) is determined. The determination may be performed by the motion trigger generator or the transmit controller may calculate the delay 608 based on the signal provided by the motion trigger generator. When the transmit controller receives an ECG trigger signal (e.g., from ECG trigger generator 410), the transmit controller will wait to acquire elastography measurements until the delay 608 has passed.

FIG. 7 illustrates an example of determining a motion trigger and a delay based on spectral Doppler flow data according to embodiments of the present disclosure. In the example screen shot 700 shown in FIG. 7, the Doppler flow data includes plot 702 of blood flow velocity data acquired at a mitral valve of a heart. The vertical axis indicates a velocity magnitude (cm/s) and the horizontal axis indicates time(s). Above the Doppler flow data is an ECG trace 704 plotted over time. As shown in FIG. 7, after the R-wave 706 appears on the ECG trace 704, velocity magnitudes of blood flow dramatically increase as the heart enters systole. After a delay 708 from the R-wave 706, the heart enters diastasis 710, where velocity values are at a minimum, that is, when blood flow through the mitral valve is at a minimum.

In an ultrasound imaging system where elastography measurements are acquired based solely on a motion-based trigger, such as motion trigger generator 450, the blood flow velocity data shown in plot 702 may be analyzed to determine when the heart is at rest. The determination may be based on when the velocity and/or a slope of the velocity curve (e.g., acceleration) falls below a threshold value. Once the heart is determined to be at rest, a motion trigger signal is sent to a transmit controller, which will then cause an ultrasound transducer to acquire elastography measurements of the heart.

In an ultrasound imaging system where elastography measurements are acquired based on a modified ECG trigger signal, the velocity data shown in plot 702 may be analyzed to determine when the heart is at rest, similar to the method described in the previous paragraph. Once the heart is determined to be at rest, the delay 708 between the R-wave 706 and the resting state (e.g., diastasis 710) is determined. The determination may be performed by the motion trigger generator or the transmit controller may calculate the delay 708 based on the signal provided by the motion trigger generator. When the transmit controller receives an ECG trigger signal (e.g., from ECG trigger generator 410), the transmit controller will wait to acquire elastography measurements until the delay 708 has passed.

Figure 8:
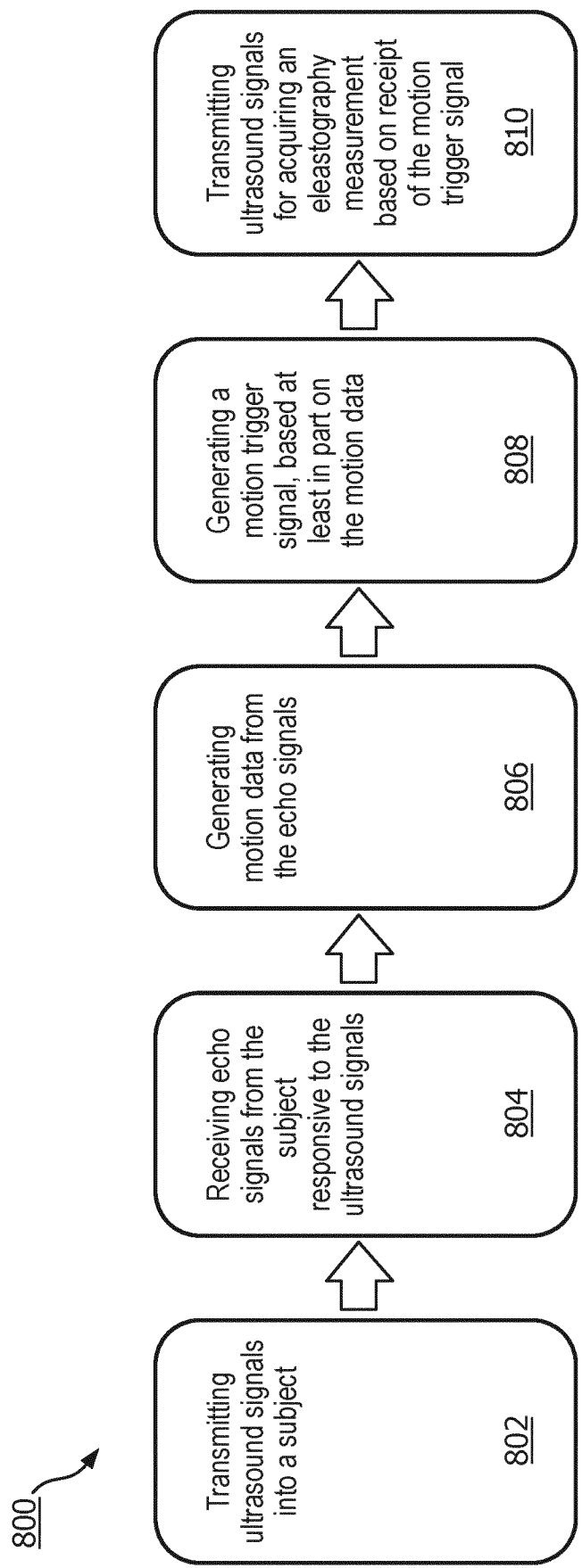
FIG. 8 is a flowchart of a method according to embodiments of the present disclosure.

FIG. 8 shows a flow diagram of a method 800 according to principles of the present disclosure. The method 800 may be a method of acquiring elastography measurements. At block 802, "transmitting ultrasound signals into a subject" is performed. The transmitting may be performed with an ultrasound probe. More specifically, with a transducer array included in the ultrasound probe. For example ultrasound probe 412 and transducer array 414 shown in FIG. 4. At block 804, "receiving echo signals from the subject responsive to the ultrasound signals" is performed. The receiving may also be performed by the ultrasound probe. At block 806, "generating motion data from the echo signals," may be performed. In some embodiments, generating motion data may be performed by a motion processor, such as motion processor 448, shown in FIG. 4. In some embodiments, motion processor 448 may be a Doppler processor. At block 808, "generating a motion trigger signal, based at least in part on the motion data," may be performed. Generating the motion trigger signal may be performed by a motion trigger generator, such as motion trigger generator 450 shown in FIG. 4. At block 810, "transmitting ultrasound signals for acquiring an elastography measurement when the motion trigger signal is received," is performed. The transmitting may be performed by the ultrasound probe under the control of a transmit controller that receives the motion trigger signal, for example, transmit controller 420 shown in FIG. 4.

In various embodiments where components, systems and/or methods are implemented using a programmable device, such as a computer-based system or programmable logic, it should be appreciated that the above-described systems and methods can be implemented using any of various known or later developed programming languages, such as "C", "C++", "FORTRAN", "Pascal", "VHDL" "Verilog" and the like. Accordingly, various storage media, such as magnetic computer disks, optical disks, electronic memories and the like, can be prepared that can contain information that can direct a device, such as a computer, to implement the above-described systems and/or methods. Once an appropriate device has access to the information and programs contained on the storage media, the storage media can provide the information and programs to the device, thus enabling the device to perform functions of the systems and/or methods described herein. For example, if a computer disk containing appropriate materials, such as a source file, an object file, an executable file or the like, were provided to a computer, the computer could receive the information, appropriately configure itself and perform the functions of the various systems and methods outlined in the diagrams and flowcharts above to implement the various functions. That is, the computer could receive various portions of information from the disk relating to different elements of the above-described systems and/or methods, implement the individual systems and/or methods and coordinate the functions of the individual systems and/or methods described above.

In view of this disclosure, it is noted that the various methods and devices described herein can be implemented in hardware, software and firmware. Further, the various methods and parameters are included by way of example only and not in any limiting sense. In view of this disclosure, those of ordinary skill in the art can implement the present teachings in determining their own techniques and needed equipment to affect these techniques, while remaining within the scope of the invention. The functionality of one or more of the processors described herein may be incorporated into a fewer number or a single processing unit (e.g., a CPU) and may be implemented using application specific integrated circuits (ASICs) or general purpose processing circuits which are programmed responsive to executable instruction to perform the functions described herein, for example, as described with reference to FIG. 9.

As will be appreciated, the present methods, systems, and apparatuses may be applied to existing imaging systems such as, for example, ultrasonic imaging systems provided by PHILIPS ultrasound, which may, for example, also support ARF-based SWE imaging. Certain additional advantages and features of this invention may be apparent to those skilled in the art upon studying the disclosure, or may be experienced by persons employing the novel system and method of the present invention, chief of which is the reduction of temporally and spatially dependent biases during cardiac elastography and/or inaccuracies due to motion overlay, by ultrasound imaging systems and method of operation thereof is provided. Another advantage of the present systems and method is that conventional medical imaging systems may be easily upgraded to incorporate the features and advantages of the present systems, devices, and methods. Of course, it is to be appreciated that any one of the above embodiments or processes may be combined with one or more other embodiments and/or processes or be separated and/or performed amongst separate devices or device portions in accordance with the present systems, devices and methods.

Finally, the above-discussion is intended to be merely illustrative of the present system and should not be construed as limiting the appended claims to any particular embodiment or group of embodiments. Thus, while the present system has been described in particular detail with reference to exemplary embodiments, it should also be appreciated that numerous modifications and alternative embodiments may be devised by those having ordinary skill in the art without departing from the broader and intended spirit and scope of the present system as set forth in the claims that follow. Accordingly, the specification and drawings are to be regarded in an illustrative manner and are not intended to limit the scope of the appended claims.

What is claimed is:

1. An ultrasound imaging system comprising:
    an ultrasound probe configured to transmit at least one ultrasound signal and receive at least one echo signal responsive to the ultrasound signals;
    a motion processor configured to generate motion data from the at least one echo signal;
        a motion trigger generator configured to generate a motion trigger signal based, at least in part, on the motion data;
        an electrocardiography trigger generator configured to generate an electrocardiography trigger signal based on a detection of a feature in an electrocardiography trace; and
            a transmit controller configured to cause the ultrasound probe to acquire at least one elastography measurement based on the motion trigger signal,
    wherein the transmit controller is configured to receive the electrocardiography trigger signal, and, upon receipt of the electrocardiography trigger signal, to cause the ultrasound probe to acquire the at least one elastography measurement after a delay, the delay being based on the motion trigger signal.

2. The ultrasound imaging system of claim 1, wherein the feature in the electrocardiography trace is an R-wave.

3. The ultrasound imaging system of claim 1, wherein the electrocardiography trigger signal is used to synchronize B-mode images acquired by the ultrasound probe to a cardiac cycle.

4. The ultrasound imaging system of claim 1, wherein the delay is determined automatically by the transmit controller.

5. The ultrasound imaging system of claim 1, further comprising a display configured to provide the motion data; and
    a user interface including a user control, wherein the delay is based on a user input received via the user control based on the motion data provided on the display.

6. The ultrasound imaging system of claim 1, wherein the motion data is acquired at a first location of a subject and the elastography measurement is acquired at a second location of the subject different from the first location.

7. The ultrasound imaging system of claim 1, wherein the motion trigger generator generates the motion trigger signal when the motion data indicates a portion of a subject scanned by the ultrasound probe is at rest.

8. The ultrasound imaging system of claim 7, wherein the portion of the subject is at rest when a motion related parameter indicated by the motion data is below a threshold value.

9. The ultrasound imaging system of claim 8, further comprising a user interface including a user control, wherein the threshold value is set by a user via the user control.

10. The ultrasound imaging system of claim 8, wherein the portion of the subject is at rest when the motion related parameter is below the threshold value for a given period of time.

11. The ultrasound imaging system of claim 8, wherein the motion related parameter is at least one of a velocity, an acceleration, or a flow rate.

12. The ultrasound imaging system of claim 1, wherein the motion data comprises at least one of displacement data, spectral data, or strain rate data.

13. The ultrasound imaging system of claim 1, further comprising a display configured to provide the motion data and the at least one elastography measurement.

14. A method comprising:
    transmitting, with an ultrasound probe, at least one ultrasound signals into a subject;
    receiving, with the ultrasound probe, at least one echo signals from the subject responsive to the ultrasound signals;
    generating motion data from the echo signals;
    generating a motion trigger signal, based at least in part on the motion data; generating an electrocardiography trigger signal, based at least in part on a detection of a feature of an electrocardiography trace; and
    acquiring, with the ultrasound probe, an elastography measurement based on the motion trigger signal,
        wherein the acquiring of the elastography measurement is performed after a delay following receipt of the electrocardiography trigger signal, wherein the delay is based on the motion trigger signal.

15. The method of claim 14, further comprising:
    arranging B-mode image acquired by the ultrasound probe based, at least in part, on the electrocardiography trigger signal.

* * * * *